(12) United States Patent
Kang et al.

(10) Patent No.: US 8,981,100 B2
(45) Date of Patent: Mar. 17, 2015

(54) USE OF NOVEL COUMARINS AS GLUTATHIONE AND THIOL LABELS

(75) Inventors: Hee Chol Kang, Eugene, OR (US); Kyle Gee, Springfield, OR (US); Iain Johnson, Eugene, OR (US); Michael Janes, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 1343 days.

(21) Appl. No.: 12/666,256

(22) PCT Filed: Jul. 24, 2008

(86) PCT No.: PCT/US2008/071085
§ 371 (c)(1),
(2), (4) Date: Nov. 13, 2010

(87) PCT Pub. No.: WO2009/018112
PCT Pub. Date: Feb. 5, 2009

(65) Prior Publication Data
US 2011/0045503 A1     Feb. 24, 2011

Related U.S. Application Data

(60) Provisional application No. 60/952,527, filed on Jul. 27, 2007.

(51) Int. Cl.
    C07D 491/16     (2006.01)
    C07D 491/00     (2006.01)
    G01N 33/52      (2006.01)
(52) U.S. Cl.
    CPC .................................. C07D 491/16 (2013.01)

USPC ............. 546/66; 514/288; 435/7.24; 435/7.1; 435/7.21; 436/106; 436/120

(58) Field of Classification Search
    USPC ............................................. 546/66; 514/288
    See application file for complete search history.

(56) References Cited

U.S. PATENT DOCUMENTS

| 4,711,955 A   | 12/1987 | Ward et al. |
| 5,047,519 A   | 9/1991  | Hobbs et al. |
| 5,151,517 A * | 9/1992  | Reveilleau et al. ............. 546/66 |
| 5,773,227 A   | 6/1998  | Kuhn et al. |

FOREIGN PATENT DOCUMENTS

| WO | WO-89/12052    | 12/1989 |
| WO | WO9304192      | * 3/1993 |
| WO | WO-2005065241  | 7/2005 |

(Continued)

OTHER PUBLICATIONS

Whitaker; "p-Toluenesulfonyl chloride" in "Handbook of Reagents for Organic Synthesis, Activating Agents and Protecting Groups", 1999, Wiley, pp. 394-399.*

(Continued)

*Primary Examiner* — John Mabry
*Assistant Examiner* — Daniel Carcanague
(74) *Attorney, Agent, or Firm* — Life Technologies Corporation

(57) ABSTRACT

Fluorescent quinolizinocoumarin compounds substituted with electrophilic reactive groups that bind thiol compounds are described. The compounds are useful in detecting oxidative stress and processes associated therewith in live cells.

26 Claims, 7 Drawing Sheets

(56) References Cited

FOREIGN PATENT DOCUMENTS

| WO | WO-2006023821 | 3/2006 |
|---|---|---|
| WO | WO-2009/018112 A2 | 2/2009 |

OTHER PUBLICATIONS

Silverman; "The Organic Chemistry of Drug Design and Drug Action", 1992, Academic Press, p. 325.*

Roberts; "Basic Principles of Organic Chemistry", Second Edition, 1977, p. 231.*

Goryaeva ; Proceedings of SPIE—The International Society for Optical Engineering, 1995, 2619,166-174.*

Bouizar, Z. et al., "Purification and Characterization of Calcitonin Receptors in Rat Kidney Membranes by Covalent Cross-Linking Techniques.", Eur J Biochem, vol. 155, No. 1, pp. 141-147 (1986).

Browning, J. et al., "Studies on the Differing Effects of the Tumor Necrosis Factor and Lymphotoxin on the Growth of Several Human Tumor Lines", The Journal of Immunology vol. 143, No. 6, pp. 1859-1867 (1989).

Chaurasia, C. S., "Synthesis and fluorescent properties of a new photostable thiol reagent BACM", Journal of Heterocyclic Chemistry, vol. 27, pp. 727-733 (1990).

James, Andrew M. et al., "Interactions of Mitochondria-targeted and Untargeted Ubiquinones with the Mitochondrial Respiratory Chain and Reactive Oxygen Species", The Journal of Biological Chemistry, vol. 280, No. 22, pp. 21295-21312 (2005).

Joshi, S. et al., "ATP Synthase complex from Bovine Heart Mitochondria. Subunit Arrangements as Revealed by Nearest Analysis and Susceptibility to Trypsin", The Journal of Biological Chemistry, vol. 256, No. 25, pp. 14518-14525 (1990).

Jung, S. M. et al., "Crosslinking of Platelet Glycoprotein lb by N-Succinimidyl (4-azidophenyldithio) Propionate and 3, 3'-dithiobis (Sulfosuccinimidyl Promionate)", Biochimica et Biophysica Acta, vol. 761, No. 2, pp. 152-162 (1983).

Park, L. S. et al., "Characterization of the Cell Surface Receptor for a Multi-Lineage Colony-Stimulating Factor (CSF-2alpha)", The Journal of Biological Chemistry vol. 261, No. 1, pp. 205-210 (1986).

PCT/US2008/071085, "International Preliminary Report on Patentability mailed on Feb. 11, 2010", pp. 1-7.

PCT/US2008/071085, "International Search Report and Written Opinion mailed Jun. 2, 2009", pp. 1-12.

Ross, M. F. et al., "Lipophilic Triphenylphosphonium Cations as Tools in Mitochondrial Bioenergetics and Free Radical Biology", Biochemistry (Moscow) vol. 70, No. 2, pp. 273-283 (2005).

Tauskela, J. S. et al., "Evaluation of glutathione-sensitive fluorescent dyes in cortical culture", GLIA, vol. 30, No. 4, pp. 329-341 (2000).

Tod, M. et al., "Chromatographic and Luminescence Properties of A 7-Aminocoumarin Derivative with Peroxyoxalate Chemiexcitation", Analytica Chemica Acta, vol. 223, pp. 309-317 (1989).

Traore, F. et al., "Determination of malonaldehyde by coupled high-perormance liquid chromatography-spectrofluorimetry after derivatization with luminarin 3", J. Chromatography, vol. 648, No. 1, pp. 111-118, (1993).

Zarling, D. A. et al., "Mapping of Lymphocyte Surface Polypeptide Antigens by Chemical Cross-Linking with BSOCOES", The Journal of Immunology, vol. 124, No. 2, pp. 913-920 (1980).

* cited by examiner

Example 2

Example 1

CMAC mBCl

USE OF NOVEL COUMARINS AS GLUTATHIONE AND THIOL LABELS

CROSS-REFERENCE TO RELATED APPLICATIONS

This application claims priority to U.S. Ser. No. 60/952,527, filed Jul. 27, 2007, which disclosure is herein incorporated by reference.

FIELD OF THE INVENTION

Described herein are indicators of reactive thiol species, such as glutathione (GSH), which are involved in a myriad of biological pathways and pathologies involving oxidative stress and cellular apoptosis.

BACKGROUND OF THE INVENTION

Thiol compounds play a principal role in maintaining the appropriate oxidation-reduction state of proteins, cells and organisms. Thiols present in biological systems include glutathione, cysteine, N-acetylcysteine (AcCSH), and protein thiols, as well as the contribution of these components to symmetric and mixed disulfides.

Glutathione is the principal intracellular non-protein thiol and plays a major role in the maintenance of the intracellular red-ox state. Glutathione exists in a dimerized oxidized state (GSSG) and a reduced monomeric state (GSH).

Glutathione, as with other thiol compounds, is a nucleophilic scavenger and an electron donor via the sulfhydryl group. Its reducing ability maintains molecules such as ascorbate and proteins in their reduced state. Glutathione is also the cofactor for the selenium-containing glutathione peroxidases. These enzymes detoxify peroxides, such as hydrogen peroxide and other peroxides. Another antioxidant activity of glutathione is the maintenance of the antioxidant/reducing agent ascorbate in its reduced state. This is accomplished via glutathione-dependent dehydroascorbate reductase which is comprised of glutaredoxin and protein isomerase reductase. Glutathione also plays roles in catalysis, metabolism, signal transduction, gene expression and apoptosis.

Glutathione (GSH) indicators exist, including monochlorobimane (mBCl), and 4-chloromethylcoumarin (CMAC), and are traditionally used for detection of intracellular GSH as an indicator of apoptosis.

Compounds having a general quinolizinocoumarin scaffold and functionalized versions thereof have been used as fluorescent labels, such as for carbonyl or malonaldehyde detection (Traore et al. J. of Chromatography, 648(1) (1993) pgs. 111-118), glucose biosensors (WO 05/65241), detection agents for human aldo-keto 1C reductases (AKR1Cs) (WO 06/23821), and for derivatizing amines (Tod et al. Analytica Chimica Acta, 223(2) (1989) pgs 309-17).

In order to accurately detect glutathione and other thiol species in a biological sample it would be desirable to have a highly fluorescent thiol indicator compatible with biological systems.

SUMMARY OF THE INVENTION

Surprisingly, it was found that 2,3,6,7-tetrahydro-9-halomethyl-1H,5H-quinolizino(9,1-gh)coumarin compounds provide for highly fluorescent cellular indicators of thiol compounds, particularly glutathione (GSH).

Thus, In certain embodiments, the present compounds include, a 2,3,6,7-tetrahydro-9-halomethyl-1H,5H-quinolizino(9,1-gh)coumarin, wherein halo is bromo or chloro. In certain aspects the coumarin is further substituted with a cationic group, wherein the cationic group comprises a triphenylphosphonium ion.

In another embodiment, the present coumarin compounds are according to Formula (I) or a salt or tautomer thereof:

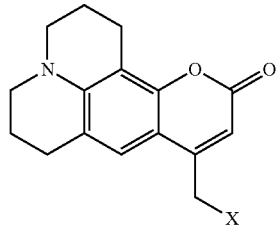

I wherein,
X is an electrophilic reactive group that does not comprise a carbonyl group; or
X is a substituted thiol group.
In one aspect X is halo, including but not limited to bromo and chloro. In a further aspect X is a tosyl, brosyl or mesyl group. In another aspect X is a substituted thiol group.
In another embodiment the present compounds are used in a method for detecting or quantifying a thiol compound in a sample, the method comprising:
(a) contacting the sample with 2,3,6,7-tetrahydro-9-halomethyl-1H,5H-quinolizino(9,1-gh)coumarin, to form a contacted sample;
(b) incubating the contacted sample for an appropriate amount of time to form an incubated sample;
(c) illuminating the incubated sample with an appropriate wavelength to form an illuminated sample; and
(d) detecting fluorescent emissions from the illuminated sample;
wherein the fluorescent emissions are used to detect or quantify the thiol compound in the sample.

In yet another embodiment the present invention provides a method of synthesizing 2,3,6,7-tetrahydro-9-halomethyl-1H,5H-quinolizino(9,1-gh)coumarin comprising:
contacting 8-hydroxyjulolidine with ethyl 4-haloacetoacetate to form a reaction mixture;
incubating the reaction mixture for a sufficient amount of time for 2,3,6,7-tetrahydro-9-halomethyl-1H,5H-quinolizino(9,1-gh)coumarin to form.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Introduction:

The present invention is based on detection of thiol groups present on molecules such as glutathione (GSH) through in-situ covalent attachment of free thiol groups to an electrophilic substituent on the fluorescent quinolizinocoumarin moiety. Covalent attachment of a thiol-containing moiety such as glutathione to the quinolizinocoumarin scaffold results in an increased fluorescent response. The conjugated molecule is also separable from the unconjugated fluorophore, formaldehyde-fixable (cell-based data and figures are derived from fixed samples) and Triton X-100 resistant, thereby increasing suitability in cell-based systems.

Figure 3:
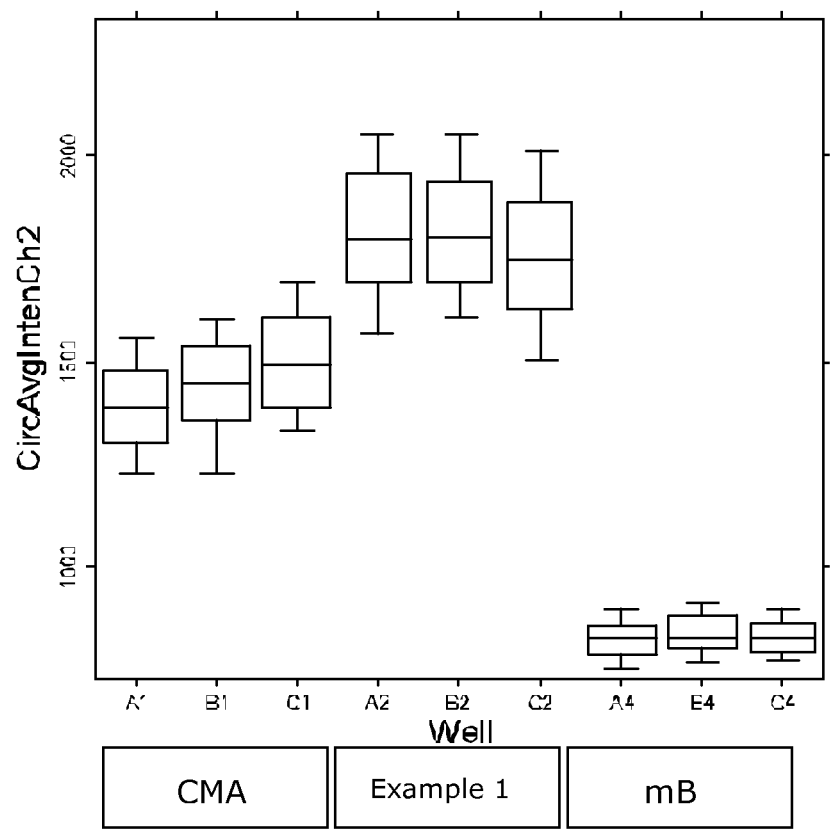
FIG. 3 shows that Example 1 is brighter than CMAC and mBCl in U-2 OS cells and dye concentration=40 uM with 30 min. staining and 3.7% formaldehyde fixation. Staining intensity measured at the nuclear region of individual cells and background level ~400.
Figure 4:
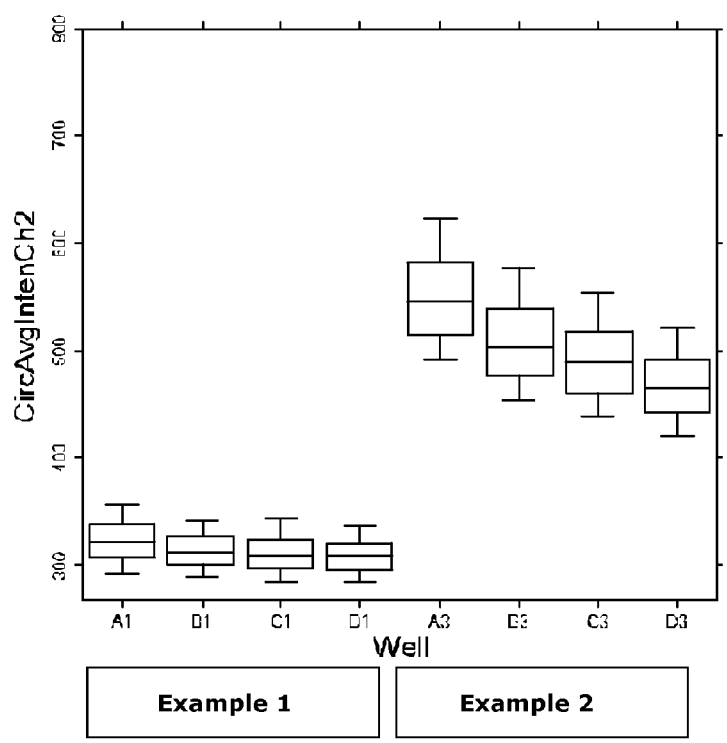
FIG. 4 shows Example 2 is brighter than Example 1 in U-2 OS cells and dye concentration=40 uM with 30 min. staining and 3.7% formaldehyde fixation. Staining intensity measured at the nuclear region of individual cells and background level ~100.
Figure 5:
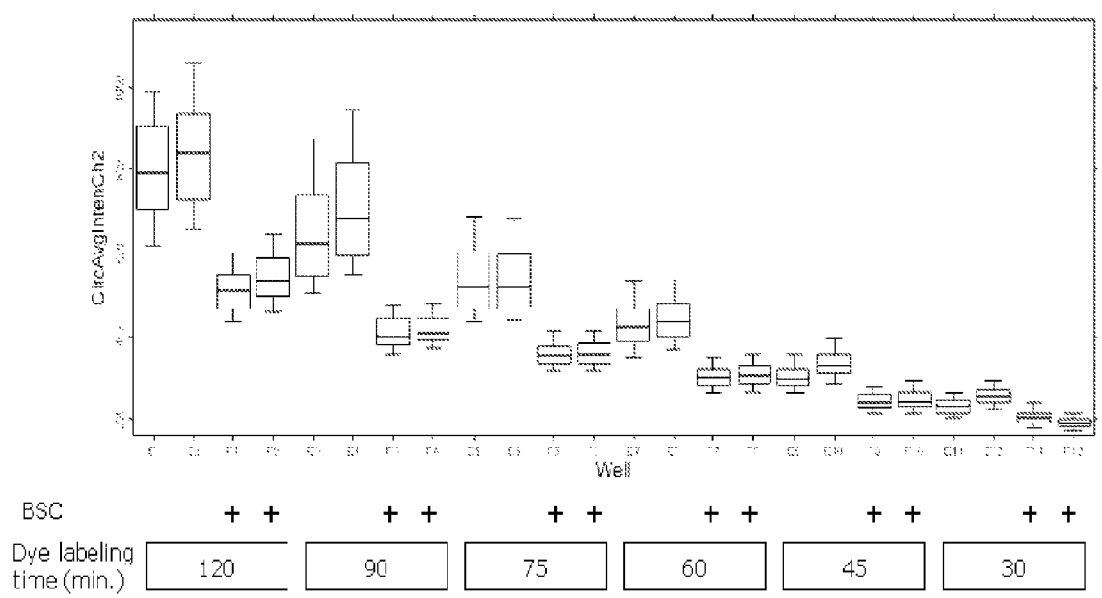
FIG. 5 shows reduction of Example 2 staining by BSO treatment (an inhibitor of glutathione biosynthesis, or a GST inhibitor) in U-2 OS cells, DL-buthionine-(S,R)-sulfoximine (BSO), 4 mM, overnight incubation with Example 2 concentration=40 uM and varied staining time with 3.7% formaldehyde fixation. Staining intensity measured at the nuclear region of individual cells with background level ~100.
Figure 6:
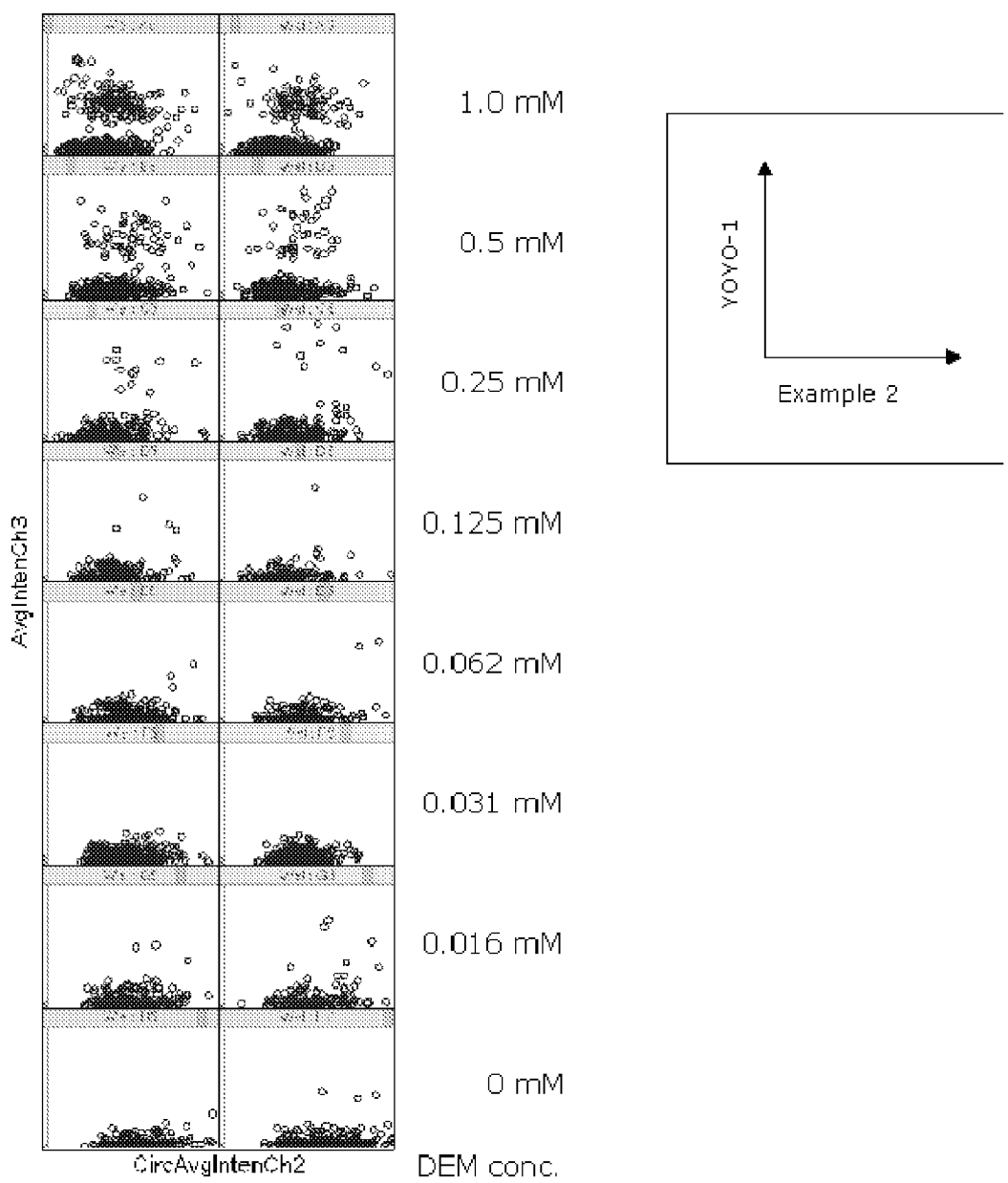
FIG. 6 shows multiplexing of Example 2 with YOYO-1; effect of Dimethyl maleate (DEM) treatment on Clone 9 cells (Rat liver cells) with DEM 1 mM, 2 hours, Example 2 40 uM/YOYO-1 1 uM, 30 min, 3.7% formaldehyde fixation staining intensity of Example 2 and YOYO-1 measured at the nuclear region of individual cells. Scatter plot trellis: two wells for each DEM concentration; X axis=Example 2 intensity; Y axis=YOYO-1 intensity. Note: decrease of Example 2 signal (left shift) and increase of YOYO-1 signal (up shift) at higher concentration of DEM.
Figure 7:
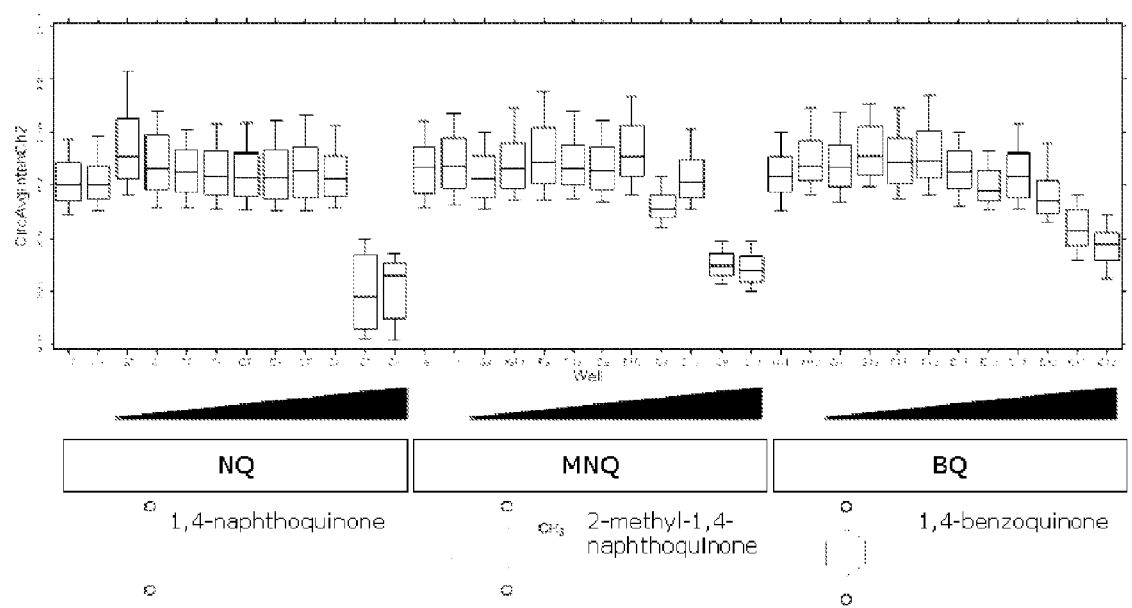
FIG. 7 shows effects of staining with Example 2 in the presence of varying concentrations of quinone toxicants (1,4-naphthoquinone (NQ), 2-methyl-1,4-naphthoquinone (MNQ) and 1,4-benzoquione (BQ)) on in U-2 OS cells (toxicant treatment occurred for 2 hours with exposure to Example 2 for 30 min and formaldehyde fixation). Staining intensity was measured at the nuclear region of individual cells and results show a decrease of staining at high toxicant concentrations. Toxicant concentrations were obtained by step gradient: steps of 1/3 with a high concentration=33.3 uM, with 2 wells for one concentration and a control (2 wells at the left for each group): no toxicant treatment.

The novel intracellular indicators described herein have optimal wavelength excitation spectra at approximately 405 nm. Wavelengths longer than UV (such as 405) can be less damaging to live cells, thus illumination of the present compounds in live cells is potentially less harmful/invasive than other know probes that are optimally excited with UV wavelengths. As evidenced by FIG. 6 (among others), the spectral properties of compounds described herein are favorable for multiplexing. Furthermore, the compound is significantly brighter than current approaches using CMAC and bimanes (FIG. 3), thereby facilitating cell-based analysis (FIGS. 5 & 7) where other approaches have questionable utility due to very dim signal and subsequent inability to discern healthy vs. GSH-compromised cells. Furthermore, the indicators are modular, whereby targeting of particular regions in the cell, such as the mitochondria, is accomplished by modifying charge and/or polarity characteristics.

Definitions:

The following are abbreviations used throughout the application:

BQ . . . 1,4-benzoquione
BSO . . . DL-Buthionine-(S,R)-sulfoximine
CMAC . . . 4-chloromethylcoumarin
DEM . . . Dimethyl maleate
DPBS . . . Dulbecco's Phosphate-Buffered Saline
DTNB . . . 5,5'-dithiobis(2-nitrobenzoic acid)
DTT . . . Dithiothreitol
GSH . . . Gluathione (reduced)
mBCl . . . monochlorobimane
MES . . . 2-(N-morpholino)ethanesulfonic acid
MNQ . . . 2-methyl-1,4-naphthoquinone
NQ . . . 1,4-naphthoquinone
PBS . . . Phosphate-Buffered Saline Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a 2,3,6,7-tetrahydro-9-halomethyl-1H,5H-quinolizino(9,1-gh)coumarin" includes a plurality of compounds having the 2,3,6,7-tetrahydro-9-halomethyl-1H, 5H-quinolizino(9,1-gh)coumarin scaffold and reference to "a cell" includes a plurality of cells and the like.

Unless defined otherwise, all technical and scientific terms used herein have the same meaning as commonly understood by one of ordinary skill in the art to which this invention is related. The following terms are defined for purposes of the invention as described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer (e.g. L-glutathione). Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^4$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "affinity" as used herein refers to the strength of the binding interaction of two molecules, such as a metal chelating compound and a metal ion or a positively charged moiety and a negatively charged moiety.

The term "aqueous solution" as used herein refers to a solution that is predominantly water and retains the solution characteristics of water. Where the aqueous solution contains solvents in addition to water, water is typically the predominant solvent.

The term "carrier molecule" as used herein refers to a biological or a non-biological component that is covalently bonded to a compound of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term "cell permeable" as used herein refers to compounds of the present invention that are able to cross the cell membrane of live cells.

The term "complex" as used herein refers to the association of two or more molecules, usually by non-covalent bonding.

The term "detectable response" as used herein refers to a change in or an occurrence of, a signal that is directly or indirectly detectable either by observation or by instrumentation and the presence or magnitude of which is a function of the presence of a target metal ion in the test sample. Typically, the detectable response is an optical response resulting in a change in the wavelength distribution patterns or intensity of absorbance or fluorescence or a change in light scatter, fluorescence quantum yield, fluorescence lifetime, fluorescence polarization, a shift in excitation or emission wavelength or a combination of the above parameters. The detectable change in a given spectral property is generally an increase or a decrease. However, spectral changes that result in an enhancement of fluorescence intensity and/or a shift in the wavelength of fluorescence emission or excitation are also useful. The change in fluorescence on ion binding is usually due to conformational or electronic changes in the indicator that may occur in either the excited or ground state of the fluorophore, due to changes in electron density at the ion binding site, due to quenching of fluorescence by the bound target metal ion, or due to any combination of these or other effects. Alternatively, the detectable response is an occurrence of a signal wherein the fluorophore is inherently fluorescent and does not produce a change in signal upon binding to a metal ion or biological compound.

The term "dye" as used herein refers to a compound that emits light to produce an observable detectable signal.

The term "fluorophore" as used herein refers to a composition that is inherently fluorescent or demonstrates a change in fluorescence upon binding to a biological compound or metal ion, or metabolism by an enzyme, i.e., fluorogenic. Fluorophores may be substituted to alter the solubility, spectral properties or physical properties of the fluorophore. Numerous fluorophores are known to those skilled in the art and include, but are not limited to coumarin, acridine, furan, dansyl, cyanine, pyrene, naphthalene, benzofurans, quinolines, quinazolinones, indoles, benzazoles, borapolyazaindacenes, oxazine and xanthenes, with the latter including fluoresceins, rhodamines, rosamine and rhodols as well as other fluorophores described in RICHARD P. HAUGLAND, MOLECULAR PROBES HANDBOOK OF FLUORESCENT PROBES AND RESEARCH CHEMICALS ($9^{th}$ edition, including the CD-ROM, September 2002). The fluorophore moiety may be substituted by substituents that enhance solubility, live cell permeability and alter spectra absorption and emission.

"Glutathione indicator" refers to a compound whose fluorescent properties are affected, preferably increased, by the reaction glutathione.

"H" indicates hydrogen.

"Halo" or "halogen" refers to fluoro, chloro, bromo or iodo.

The term "kit" as used refers to a packaged set of related components, typically one or more compounds or compositions.

The term "Linker" or "L", as used herein, refers to a single covalent bond or a series of stable covalent bonds incorporating 1-20 nonhydrogen atoms selected from the group consisting of C, N, O, S and P that covalently attach the fluorogenic or fluorescent compounds to another moiety such as a chemically reactive group or a biological and non-biological component. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleavable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986) Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

"Patient," "subject" or "individual" refers to mammals and includes humans and non-human mammals, such as monkeys, dogs, cats, horses, cows, pocket pets, pigs or rats.

As used herein, "pro-fluor" refers to a reactive compound that undergoes conversion to a desired fluorophore within a biological system, such conversion usually involving conjugation with an analyte of interest, such as glutathione.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds., *Organic Functional Group Preparations*, Academic Press, San Diego, 1989).

"Electrophilic reactive group" refers to a reactive group as described above that is capable of reaction with a nucleophile. Preferably, the electrophilic reactive group is particularly and selectively reactive with thiol-containing molecules, such as glutathione (GSH). Exemplary electrophilic reactive groups of the present invention are halide groups, such as bromide or chloride substituents.

The term "reporter molecule" as used herein refers to a fluorophore or dye, terms that are defined above, which comprise part of the present intracellular ion indicators.

"Salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

The term "sample" as used herein refers to any material that may contain a target analyte, particularly glutathione. Typically, the sample is a live cell or a biological fluid that comprises endogenous host cell proteins. Alternatively, the sample may be a control, buffer solution or an environmental sample containing reactive thiol groups. The sample may be in an aqueous solution, a viable cell culture or immobilized on a solid or semi solid surface such as a polyacrylamide gel, membrane blot or on a microarray.

"Stereoisomer" or "stereoisomers" refer to compounds that differ in the chirality of one or more stereocenters. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moeity such as pyrazoles, imidazoles, benzimidazoles, triazoles, and tetrazoles.

"Thiol" refers to a compound —S—R, wherein R is H (sulfhydryl) or a substitution group, such as alkyl or substituted alkyl. (In normal practice thiols (—SH) are distinguished from sulfides or thioethers (—S—R where R is alkyl)).

"Thiol compound" refers to a compound comprising a thiol substituent. Exemplary thiol compounds include cysteine and peptides or proteins. One particularly preferred thiol compound of the present invention is glutathione.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Unless numbered, or proper claim construction (e.g. antecedent basis) requires it, multiple steps in a method or process claim/embodiment are not required to be performed sequentially.

The Compounds

In general, for ease of understanding the present invention, the compounds and corresponding substituents will first be described in detail, followed by the many and varied methods in which the compounds find uses, which is followed by exemplified methods of use and synthesis of certain novel compounds that are particularly advantageous for use with the methods of the present invention.

Compounds of the present invention generally comprise a quinolizinocoumarin scaffold and an electrophilic reactive group or a thiol-containing group. A preferred compound of the present invention comprises a 2,3,6,7-tetrahydro-9-halomethyl-1H,5H-quinolizino(9,1-gh)coumarin. In a more particular embodiment, halo is bromo or halo is chloro. In another embodiment, the 2,3,6,7-tetrahydro-9-halomethyl-1H,5H-quinolizino(9,1-gh)coumarin is substituted with a cationic group. More particularly, the cationic group comprises a triphenylphosphonium ion. Another preferred compound of the present invention comprises a 2,3,6,7-tetrahydro-9-thiomethyl-1H,5H-quinolizino(9,1-gh)coumarin.

Another embodiment of the invention provides a compound of Formula (I) or a salt or tautomer thereof:

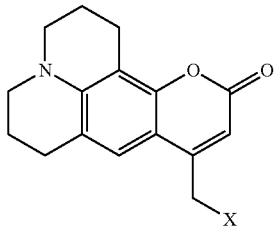

wherein,

X is an electrophilic reactive group; or

X is a substituted thiol group.

In another embodiment thereof, the electrophilic reactive group does not comprise a carbonyl group. In another embodiment, X is halo. More particularly, X is bromo. In another embodiment, X is chloro. In another embodiment, X is a tosyl, brosyl or mesyl group. In another embodiment, X is a substituted thiol group. More particularly, X is glutathione or a derivative thereof.

A preferred compound of the present invention is: 2,3,6,7-tetrahydro-9-bromomethyl-1H,5H-quinolizino(9,1-gh)coumarin. Another preferred compound of the present invention is: 2,3,6,7-tetrahydro-9-chloromethyl-1H,5H-quinolizino(9,1-gh)coumarin.

The groups provide a number of technical advantages over existing compounds, including bright fluorescent response to glutathione, selective reactivity with thiol moieties, increased internalization and thiol binding activity in the cell, modulation for increased or decreased localization in the mitochondria of the cell, preferred wavelength emissions for optimal detection, ability to multiplex with other shorter or longer wavelength indicators, and increased sensitivity for detection of cellular activities/processes.

Where the detectable response to a thiol-containing analyte is a fluorescence response, it is typically a change in fluorescence, such as a change in the intensity, excitation or emission wavelength, distribution of fluorescence, fluorescence lifetime, fluorescence polarization, change in cellular distribution of fluorescence in live cells, or a combination thereof. Preferably, the detectable optical response upon reacting with a target thiol is a change in cellular distribution of fluorescence in live cells relative to the unconjugated fluorophore in the absence of the thiol. Preferably the present compounds provide significantly enhanced fluorescence intensity over previously known compounds such as MBCl and CMAC.

The fluorescent dye portion of the present invention is the quinolizinocoumarin scaffold, which has an excitation maximum at about 405 nm. In another embodiment, the dye has an excitation maximum from about 380-420 nm, 390-415 nm or 400-410 nm. In another embodiment, the dye has an emission maximum from about 390-450 nm, 400-440 nm or 410-430 nm.

In a preferred embodiment, the compound of the present invention has the structure:

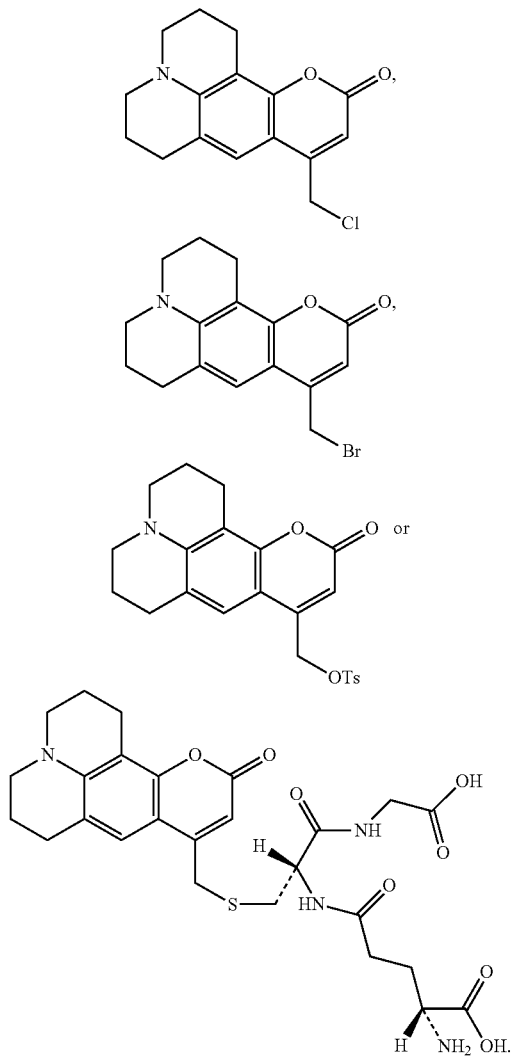

In another embodiment of the invention, the thiol indicator further comprises a reactive group, carrier molecule or solid support. These substituents can be attached to the reporter molecule, the metal chelating moiety, provided that they do not interfere with the detection of thiols, such as glutathione.

Reporter Molecules

Additional reporter molecules can be included for multiplexing with the thiol indicator compounds of the present invention. The additional reporter molecules confer a detectable signal, directly or indirectly, to other intracellular processes. This results in the ability to detect, monitor and/or quantitate a complete cellular process, cascade or pathology, or multiple processes simultaneously.

The reporter molecules can be any reporter molecule known to one skilled in the art, as long as they are separately detectable from the thiol indicators described herein. A wide variety of chemically reactive fluorescent dyes that may be suitable for incorporation into the reporter molecules of the invention are already known in the art (RICHARD P. HAUGLAND, MOLECULAR PROBES HANDBOOK OF FLUORESCENT PROBES AND RESEARCH PRODUCTS (2002)). Reporter molecules include, without limitation, a fluorophore, a dye, or a tandem dye (energy transfer pair). Preferably, the reporter molecule is a fluorophore wherein when the present compounds are non-fluorescent until bound by an analyte, i.e. fluorogenic.

Reactive Groups

The present compounds are chemically reactive, and are substituted by at least one reactive group. The reactive group functions as the site of attachment for the thiol moiety, such as glutathione. Additional reactive groups may be present to bind a carrier molecule or a solid support, wherein the reactive group chemically reacts with an appropriate reactive or functional group on the carrier molecule or solid support.

In an exemplary embodiment, the compounds of the invention comprise an electrophilic reactive group which is a member selected from an acrylamide, an activated ester of a carboxylic acid, a carboxylic ester, an acyl azide, an acyl nitrile, an aldehyde, an alkyl halide, an anhydride, a boronate, a diazoalkane, a haloacetamide, a haloalkyl, a halotriazine, an imido ester, an isocyanate, an isothiocyanate, a maleimide, a phosphoramidite, a photoactivatable group, a reactive platinum complex, a silyl halide, a sulfonyl halide, and a thiol. In a particular aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

These reactive groups are synthesized during the formation of the present compound and carrier molecule and solid support containing compounds to provide chemically reactive thiol-binding compounds. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength.

Carrier Molecules:

In any of the above embodiments, the compound can be covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an IgG binding protein, a fluorescent protein, agarose, and a non-biological microparticle.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —CH$_2$OCOalkyl and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, insulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is a cell, cellular systems, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an alternative embodiment the present compounds are bound to a carrier molecule or solid support such as a bioparticle (e.g. bacterial particles), peptides, antibodies, polymeric particles (e.g. polystyrene beads), receptor binding domains, nucleic acid binding proteins, kinase substrates, phosphatase substrates, and other carrier molecules that are useful for facilitating passive and cell mediated uptake of the present compounds or carrier molecules that are useful for localizing the present compounds such that measurement of the metal ions is indicative of the cellular events in the local environment. Examples of carrier molecules that facilitate passive and cell mediated uptake include antibodies, bioparticles, receptor binding proteins or peptides (binding domain) and the like. Examples of carrier molecules that provide useful information either for localization or because they act as an enzyme substrate include kinase substrates, phosphatase substrates, antibodies, nucleic acid binding proteins, nucleic acids and the like.

In an exemplary embodiment, the carrier molecule comprises a specific binding pair member wherein the present compounds are conjugated to a specific binding pair member and used to the formation of the bound pair. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. In this instance, the dye compounds of the present invention function as a reporter molecule for the specific binding pair. Exemplary binding pairs are set forth in Table 1.

TABLE 1

Representative Specific Binding Pairs

| antigen | Antibody |
|---|---|
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |

TABLE 1-continued

Representative Specific Binding Pairs

| antigen | Antibody |
|---|---|
| peptide | peptide receptor |
| protein | protein receptor |
| enzyme substrate | Enzyme |
| DNA (RNA) | cDNA (cRNA)† |
| hormone | hormone receptor |
| ion | Chelator |

*IgG is an immunoglobulin
†cDNA and cRNA are the complementary strands used for hybridization Solid Supports In an exemplary embodiment, the present compounds of the invention are covalently bonded to a solid support. The solid support may be attached to the compound either through the chelating moiety, reporter molecule or DYE, a substituent on the chelating moiety, reporter molecule or DYE, or through a reactive group, if present, or through a carrier molecule, if present. Even if a reactive group, reporter molecule and/or a carrier molecule are present, the solid support may be attached through the chelating moiety.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly (ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

Preparation of Conjugates

The preparation of dye conjugates using reactive dyes or linkers is well documented, e.g. by R. Haugland, MOLECULAR PROBES HANDBOOK OF FLUORESCENT PROBES AND RESEARCH CHEMICALS, Chapters 1-3 (1996); and Brinkley, BIOCONJUGATE CHEM., 3, 2 (1992). Conjugates typically result from mixing appropriate reactive dyes and the substance to be conjugated in a suitable solvent in which both are soluble. The dyes of the invention are readily soluble in aqueous solutions, facilitating conjugation reactions with most biological materials. For those reactive dyes that are photoactivated, conjugation requires illumination of the reaction mixture to activate the reactive dye.

In-Situ Formation of Conjugates:

In a preferred embodiment, compounds and compositions comprising an electrophilic reactive group passively diffuse into cells, or are actively transported, wherein the reactive group reacts with intracellular thiol groups, present on molecules such as glutathione or other cysteine-containing moieties, forming fluorescent conjugates that are well-retained and can be fixed with aldehyde fixatives. Excess unconjugated reagent and by-products passively diffuse to the extracellular medium, where they can be washed away.

The indicator-protein adducts that form in labeled cells can be retained by the cells throughout development, meiosis, and in vivo tracing. The label is inherited by daughter cells after cell division, or cell fusion, and is not transferred to adjacent cells in a population.

Method of Use:

The compounds of the invention are useful for any application where it is desirable to detect thiol groups. Particularly, the present indicator compounds are useful for detecting, monitoring, or quantitating intracellular glutathione levels. In a preferred embodiment the intracellular ion indicators are well retained in the cytosol or other discrete locations in the cell, such as the mitochondria and are optimally excitable at a wavelength of about 380 nm to about 425 nm.

Particular processes, applications, and analytes detected and/or monitored by the compounds of the present invention include:

metabolism, particularly glutathione metabolism;
transport of glutathione;
transport of glutamyl amino acids;
function of glutamyl cycle and enzymes involved therein, particularly: glutamylcysteine synthetase, glutathione synthetase, glutamyl transpeptidase, glutamyl cyclotransferase, 5-oxoprolinase and dipeptidase;
interconversion of glutathione and glutathione disulfide by glutathione oxidation, glutathione peroxidase, glutathione transhydrogenases and glutathione reductase;
conjugation of glutathione by endogenous compounds and exogenous compounds such as glutathione S-transferases;
glutathione function affected by coenzymes, radiation, oxygen toxicity, cancer and calcium metabolism;
glutathione deficiency and depletion, particularly caused by or associated with: inhibition of glutathione synthesis, mutant microorganisms deficient in glutathione synthesis and human diseases involving defects of glutathione synthesis and metabolism.

Particularly, the compounds of the present invention are particularly useful in the detection or diagnosis of diseases associated with abnormal glutathione levels.

In order for a particular indicator of the present invention to be useful for detection purposes, it must exhibit a detectable change in spectral properties upon coordination with an appropriate intracellular metal ion. Preferably the change in spectral properties is a change in fluorescence properties. More preferably, the instant indicators display an intensity increase or decrease in emission energy upon the complexation of the desired target ion.

Accordingly, one aspect of the invention provides a method for detecting or quantifying a thiol compound in a sample, the method comprising:

(a) contacting the sample with 2,3,6,7-tetrahydro-9-halomethyl-1H,5H-quinolizino(9,1-gh)coumarin or a thiol indicator described herein, to form a contacted sample;

(b) incubating the contacted sample for an appropriate amount of time to form an incubated sample;

(c) illuminating the incubated sample with an appropriate wavelength to form an illuminated sample; and (d) detecting fluorescent emissions from the illuminated sample;

wherein the fluorescent emissions are used to detect or quantify the thiol compound in the sample.

In another more particular embodiment, the sample comprises cells. In another embodiment, the contacted sample is incubated for a sufficient amount of time for the 2,3,6,7-tetrahydro-9-halomethyl-1H,5H-quinolizino(9,1-gh)coumarin to enter the cell.

In another more particular embodiment, the sample comprises live cells, intracellular fluids, extracellular fluids, sera, biological fluids, biological fermentation media, environmental sample, industrial samples, proteins, peptides, buffer solutions biological fluids or chemical reactors, blood cells, immune cells, cultured cells, muscle tissue, neurons, extracellular vesicles; vascular tissue, blood fluids, saliva, urine, water, soil, waste water, sea water; pharmaceuticals, foodstuffs or beverages.

In another more particular embodiment, the thiol compound reacts with 2,3,6,7-tetrahydro-9-halomethyl-1H,5H-quinolizino(9,1-gh)coumarin.

In another more particular embodiment, the sample is immobilized on a polymeric membrane, within a polymeric gel, on a microparticle, on a microarray, on a silicon chip, on a glass slide, on a microwell plate, and on a microfluidic chip.

In another more particular embodiment, the 2,3,6,7-tetrahydro-9-halomethyl-1H,5H-quinolizino(9,1-gh)coumarin is substituted with a cationic group and the glutathione that is detected or quantified is present in the mitochondria of the cell. More particularly, the cationic group comprises a triphenylphosphonium ion.

In another more particular embodiment, the thiol compound comprises a cysteine residue. More particularly, the thiol compound is glutathione.

In one method the present indicator compounds are incubated with the sample for a sufficient amount of time to allow the indicator compound to be either passively or by cell mediated mechanisms to be taken up by the biological cells. The sample is then incubated for a sufficient amount of time to allow the present indicator compounds to bind the target thiol compounds, such as glutathione. Once inside the cells the indicator compounds bind the thiol compounds and are well retained in the cytosol or other discrete locations of the cell, such as the mitochondria or the nucleus. The unbound molecules either diffuse out and/or can be washed free of the cells.

The specific indicator used in an assay or experiment is selected based on the desired affinity for the target thiol compound as determined by the expected concentration range in the sample, the desired spectral properties, and the desired selectivity. Initially, the suitability of a material as an indicator of thiol concentration is commonly tested by mixing a constant amount of the indicating reagent with a measured amount of the target thiol under the expected experimental conditions.

Preferred thiol indicators display a high selectivity, that is, they show a sufficient rejection of non-target nucleophiles, such as free amino groups. The interference of a non-target compound is tested by a comparable titration of the indicator with that compound. Although the preferred target compound for most indicators of the present invention is glutathione, any thiol that binds and is separable from unreacted probe or yields a discrete measurable optical property over the concentration range of interest is potentially measured using one of the indicators of this invention.

Combination of additional reporter molecules is also contemplated herein for multiplexing applications. In such applications, the additional reporter can optionally be bound by a carrier molecule, reactive group and/or solid support and can be added simultaneously, sequentially or separately to the sample of interest. Secondary thiol reactive probes are particularly useful in the methods of the present invention.

Additionally, the methods of the present invention are particularly useful when performed in conjunction with an antibody specific for the target thiol compound. Particularly the quinolizinocoumarin compound, is first added to the sample, thereby binding available reduced thiol (e.g. glutathione (GSH)) leaving only oxidized form (e.g. GSSG) for the antibody, which is subsequently added, to recognize GSSG. This provides a semi-quantitative method for measuring total cellular glutathione and the proportion of reduced vs. oxidized glutathione (GSH/GSSG).

The indicator is generally prepared for use as a detection reagent by dissolving the indicator in solution at a concentration that is optimal for detection of the indicator at the expected concentration of the target thiol compound. Modifications that are designed to enhance permeability of the indicator through the membranes of living cells, such as acetoxymethyl esters and acetates, may require the indicator to be predissolved in a water miscible organic solvent such as dimethylsulfoxide (DMSO) before addition to a cell suspension, where the indicators then readily enter the cells. Intracellular enzymes cleave the esters to the more polar acids and phenols that are then well retained inside the cells.

Therefore, a method for binding and detecting target ions in a live cell comprises the following steps:
  a) contacting a sample of live cells with an indicator compound;
  b) incubating the sample and the compound for sufficient time to allow the compound to enter live cells and bind the thiol compound; and,
  c) illuminating the sample with an appropriate wavelength to generate a detectable fluorescent signal whereby the thiol compound is detected in a live cell.

A preferred indicator of the present invention for the detection and/or quantification of a desired target thiol compound, binds the target thiol compound and results in a detectable change in spectral properties. Preferably, the change in spectral properties is a detectable fluorescence response.

The optical response of the indicating reagent is determined by changes in absorbance or fluorescence, preferably fluorescence. If absorbance measurements are used to determine thiol compound concentrations, then it is usually optimal to adjust the optical density of the indicator in the sample over the range of thiol concentration to a value of approximately 0.02 to 2.5 (most preferably 0.1 to 1). For fluorescence measurements, the concentration of the indicator will depend mostly on the sensitivity of the equipment used for its detection, which may include but is not limited to fluorescence microscope, automated fluorescence imager, flow cytometer, and microplate fluorometer.

If the optical response of the indicator will be determined using fluorescence measurements, samples are typically stained with indicator concentrations of $10^{-9}$ M to $10^{-2}$ M. The most useful range of analyte (thiol compound) concentration is about one log unit above and below the dissociation constant of the thiol-indicator complex. This dissociation constant is determined by titration of the indicator with a known concentration of the target analyte, usually over the range of virtually zero concentration to approximately 100 millimolar of the target thiol, depending on which thiol compound is to be measured and which indicator is being used. The dissociation constant may be affected by the presence of other thiols, particularly cysteine containing molecules that have free sulfhydryl groups. It may also be affected by other conditions such as ionic strength, pH, temperature, viscosity, presence of organic solvents and incorporation of the indicator in a membrane or polymeric matrix, or conjugation or binding of the indicator to a protein or other biological molecule, such as albumin. Any or all of these effects need to be taken into account when calibrating an indicator.

The indicator is combined with a sample in a way that will facilitate detection of the target thiol compound concentration in the sample. The sample is generally a representative cell population, fluid or liquid suspension that is known or suspected to contain the target thiol compound. Representative samples include intracellular fluids such as in blood cells, cultured cells, muscle tissue, neurons and the like; extracellular fluids in areas immediately outside of cells; in vesicles; in vascular tissue of plants and animals; in biological fluids such as blood, saliva, and urine; in biological fermentation media; in environmental samples such as water, soil, waste water and sea water; in industrial samples such as pharmaceuticals, foodstuffs and beverages; and in chemical reactors.

The end user will determine the choice of the sample and the way in which the sample is prepared. For example the sample may include a mixture of cells, prepared for HTS. imaging, or flow cytometry. The sample includes, without limitation, any biological derived material that is thought to contain target thiol compounds, preferably glutathione. Alternatively, samples also include material that target thiol compounds have been added to determine the effect the thiol compounds have on predetermined biological parameters.

Quantification of target thiol compound levels in samples is typically accomplished using the indicators of the present invention by methods known in the art. For example, the ratiometric measurement of thiol compound concentration provides accurate measurement of thiol concentrations by the treatment of the fluorescence data as the ratio of excitation or fluorescence intensities at two wavelengths, rather than the absolute intensity at a single wavelength. Using the ratio method, a number of variables that may perturb the thiol concentration measurements are eliminated. In particular, thiol-dependent factors that affect the signal intensity, such as nonuniform intracellular dye concentrations, probe leakage, dye bleaching and cell thickness, are canceled in the ratio measurements, since these parameters have a similar effect on intensities at both wavelengths. While the ratio method can be used to determine concentrations using observation of either the excitation spectra of the indicator, the emission spectra of the indicator, or both, in the case of the indicators of the present invention, the shift in excitation energy upon binding thiol compounds makes observation of the excitation spectrum a more useful technique. In either case, to achieve maximal utility, the indicator must be calibrated (to compensate for variance in the dissociation constant of the indicator due to ionic strength, viscosity, or other conditions within the sample).

The optical response of the indicator to the target thiol compound can be detected by various means that include measuring absorbance or fluorescence changes with an instrument, visually, or by use of a fluorescence sensing device. Several examples of fluorescence sensing devices are known, such as fluorometers, fluorescence microscopes, laser scanners, flow cytometers, and microfluidic devices, as well as by cameras and other imaging equipment. Additional tools are described in the illumination section provided herein.

Targeted Probes:

In one embodiment of the invention, the sample contains cells, and the indicator is combined with the sample in such a way that the indicator is present within the sample cells. By selection of the appropriate substituents, indicators are prepared that will selectively localize in desired locations and organelles, and provide measurements of the target thiol compound in those organelles. Conjugates of the indicators of the invention with organelle-targeting peptides are used to localize the indicator to the selected organelle, facilitating measurement of target ion presence or concentration within the organelle (as described in U.S. Pat. No. 5,773,227). Alternatively, selection of a fluorophore having predominantly lipophilic substituents, wherein the lipophilic substituents are not labile, will result in localization in lipophilic environments in the cell, such as cell membranes. In a preferred embodiment, the indicator is functionalized with cationic substituents, thereby locating it in the mitochondria of the cell.

Accordingly, in a particular embodiment of the invention, the indicator of the present invention targets the mitochondria for detection of mitochondrial proteins under oxidative stress. Preferably, the mitochondria targeted compounds comprise a triphenylphosphonium group with added positive charge and hydrophobicity.

Typically, mitochondrial GSH is separately regulated from cytoplasmic and nuclear pools and must be transported into the mitochondria. Mitochondrial GSH plays an important role in normal mitochondrial function as well as protection during oxidative stress, toxicity, apoptosis, etc. and has been shown to be depleted in various pathologies such as liver cirrhosis associated with alcoholism as well as diabetic nephropathy.

Accordingly, the GSH indicators of the present invention are particularly useful in detecting, identifying, monitoring or diagnosing diseases associated with mitochondrial glutathione.

The preferred compounds of the present invention used for detecting mitochondrial GSH have the following structure:

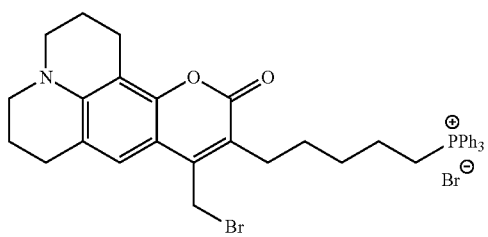

-continued

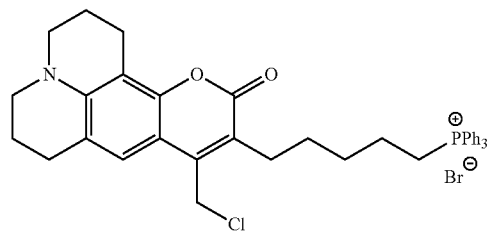

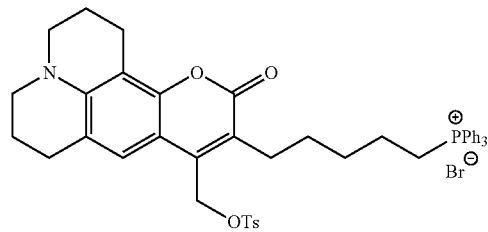

Kits of the Invention:

Due to the advantageous properties and the simplicity of use of the present thiol indicators, they are particularly useful in the formulation of a kit for the complexing, detection, quantification or monitoring of selected target thiol compounds, such as glutathione, comprising one or more compounds or compositions of the invention in any of the embodiments described above (optionally in a stock solution), instructions for the use of the compound to complex or detect a desired target thiol compound, and optionally comprising additional components.

A particular kit for binding an intracellular metal ion in a sample, comprises:

a 2,3,6,7-tetrahydro-9-halomethyl-1H,5H-quinolizino(9,1-gh)coumarin and one or more components selected from the group consisting of a calibration standard of an intracellular thiol compound, a fluorescent standard, an aqueous buffer solution and an organic solvent.

A kit of the present invention for binding a target metal thiol compound in a sample may comprise an indicator compound as described herein and instructions for use thereof. The kit may further comprise one or more components selected from the group consisting of a calibration standard of a thiol compound, a fluorescent standard, an aqueous buffer solution, control cells, an organic solvent and positive control drugs for cellular GSH depletion studies.

The additional kit components may be selected from, without limitation, calibration standards of a target ion, ionophores, fluorescence standards, aqueous buffers, control cells and organic solvents. The additional kit components are present as pure compositions, or as aqueous solutions that incorporate one or more additional kit components. Any or all of the kit components optionally further comprise buffers.

Illumination:

In a typical detection method, at any time after or during binding of the compounds of the present invention with the target metal ion, the sample is visualized whereby the compound is detected. Visualization can comprise different methods and is dependent on the fluorescent dye portion of the indicator molecule(s). Visualization typically comprises illumination with a wavelength of light capable of exciting the dye to produce a detectable optical response, as defined above, and observed with a means for detecting the optical response. Equipment that is useful for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence-based microplate readers, standard or minifluorometers, flow cytometers or chromatographic detectors. The degree and/or location of binding, compared with a standard or expected response, indicates whether and to what degree the sample possesses a given characteristic, i.e., cell processes/activity.

The optical response is optionally detected by visual inspection, or by use of any of the following devices: CCD cameras, video cameras, photographic film, laser-scanning devices, fluorometers, photodiodes, quantum counters, epifluorescence microscopes, scanning microscopes, fluorescence-based microplate readers, or by a means for amplifying the signal such as photomultiplier tubes.

As described above, while a wide variety of methods of detection are used with the present invention, a preferred method includes the use of fluorescence. Fluorescence from the compound binding to the target metal ion can be visualized with a variety of imaging techniques, including ordinary light or fluorescence microscopy.

Synthesis:

A particular aspect of the invention provides a method of synthesizing 2,3,6,7-tetrahydro-9-halomethyl-1H,5H-quinolizino(9,1-gh)coumarin comprising:

contacting 8-hydroxyjulolidine with ethyl 4-haloacetoacetate to form a reaction mixture;

incubating the reaction mixture for a sufficient amount of time for 2,3,6,7-tetrahydro-9-halomethyl-1H,5H-quinolizino(9,1-gh)coumarin to form.

In a more particular embodiment, the incubating step comprises heating the reaction mixture to at least 100° C.

In another embodiment, the reaction mixture further comprises a Lewis acid. More particularly, the Lewis acid is aluminum chloride ($AlCl_3$).

A particular synthetic scheme for preparation of the compounds of the present invention is provided in Scheme I.

Scheme I:

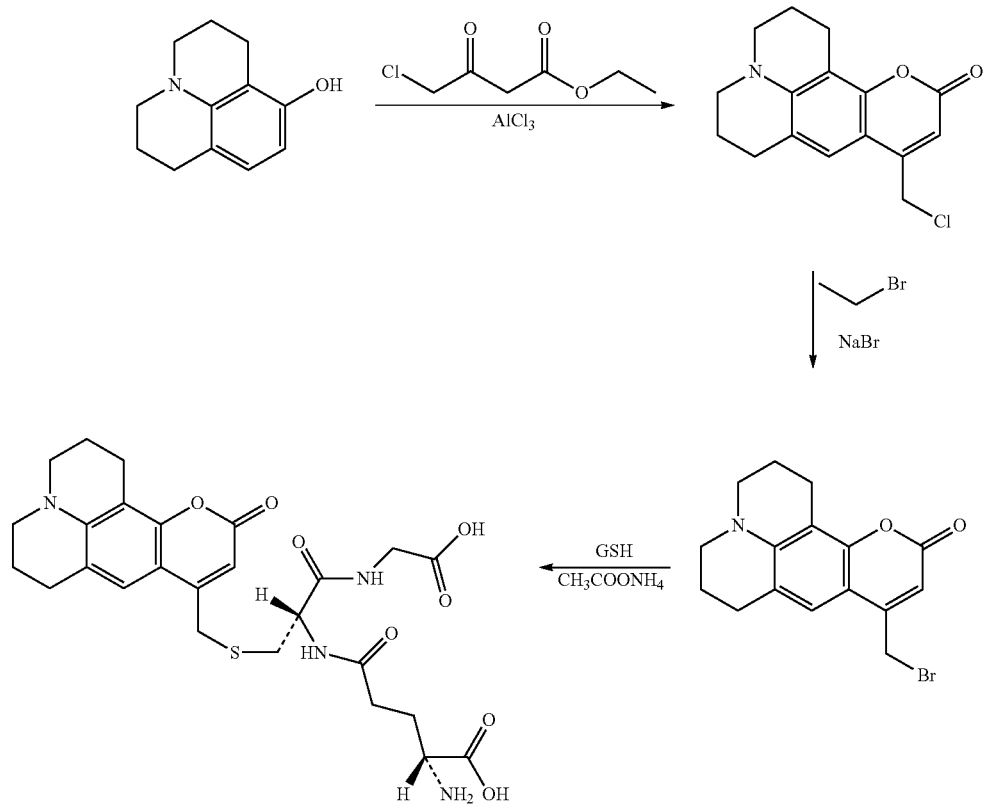

Thus, it is contemplated by the present invention that a wide variety of instrumentation may be used to detect target thiol compounds.

An additional synthetic scheme for preparation of mitochondria-targeting compounds of the present invention is provided in Scheme II.

Scheme II:

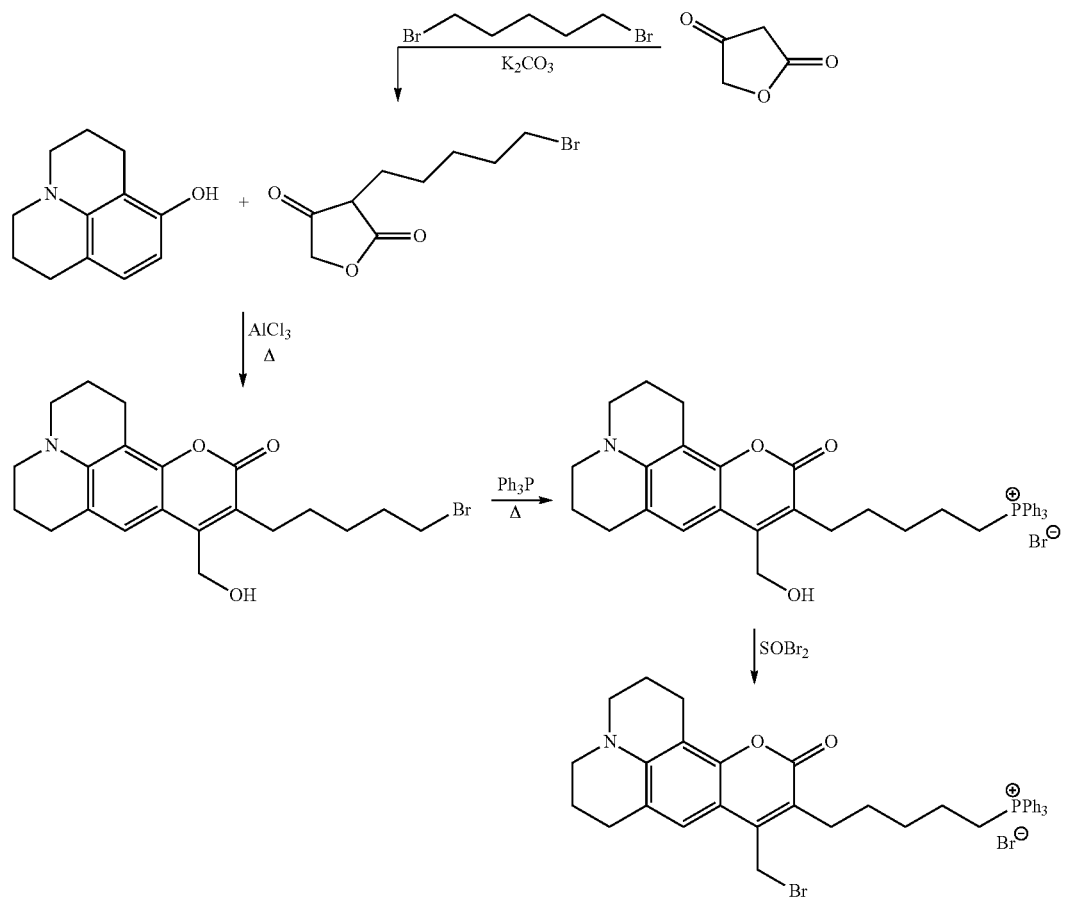

Additional synthetic methods contemplated as part of the present invention are provided in the following Examples section.

The present invention will be understood more readily by reference to the following examples, which are provided by way of illustration and are not intended to be limiting of the present invention.

EXAMPLES

Referring to the examples that follow, compounds of the present invention were synthesized using the methods described herein, or other methods, which are known in the art.

Example 1

Synthesis of 2,3,6,7-tetrahydro-9-chloromethyl-1H, 5H-quinolizino(9,1-gh)coumarin

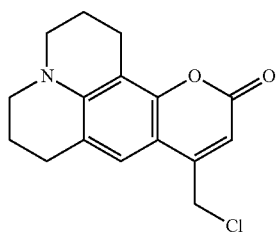 [SMILES: O=c1cc(CCl)c2cc3c4c(c2o1)CCCN4CCC3]

A mixture of 8-hydroxyjulolidine (300 mg, 1.59 mmol) and ethyl 4-chloroacetoacetate (260 ul, 1.90 mmol) was stirred at ~90° C. under argon atmosphere. To this mixture was added a solution of aluminum chloride (420 mg, 3.2 mmol) in nitrobenzene (5 ml) and the whole reaction mixture was stirred at ~130° C. for 3 hours. After the reaction mixture was cooled to room temperature, it was purified by column chromatography over silica gel eluting first with 5% ethyl acetate in hexane and then with chloroform to obtain the desired product as a yellow-brown solid (200 mg, 43% yield). TLC: $R_f$=0.56 (silica gel, 1:1 hexane/ethyl acetate). $^1$NMR (DMSO-$d_6$): chemical shift (ppm) 7.21 (s, 1H, ArH), 6.15 (s, 1H, ArH), 4.86 (s, 2H, $CH_2$), 3.28-3.25 (m, 4H, $CH_2$), 2.76-2.69 (m, 4H, $CH_2$), 1.90-1.87 (m, 4H, $CH_2$). absorption maximum: 405 nm in methanol, emission maximum: 493 nm in methanol. MS: m/e 290.20.

Example 2

Synthesis of 2,3,6,7-tetrahydro-9-bromomethyl-1H, 5H-quinolizino(9,1-gh)coumarin

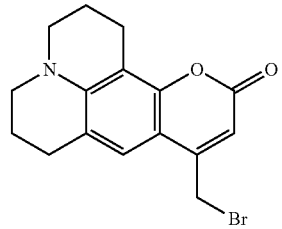 [SMILES: O=c1cc(CBr)c2cc3c4c(c2o1)CCCN4CCC3]

A mixture of 2,3,6,7-tetrahydro-9-chloromethyl-1H,5H-quinolizino(9,1-gh)coumarin (100 mg, 0.345 mmol), bromoethane (260 ul, 3.45 mmol) and sodium bromide (7 mg, 0.07 mmol) in N-methyl-2-pyrrolidine was stirred at ~65° C. for one day. The reaction mixture was cooled to room temperature and the resulting crude product was purified by column chromatography over silica gel eluting first with hexanes followed by 20% ethyl acetate in hexanes to yield the desired product as a yellow-brown solid (60 mg, 50% yield). TLC: $R_f$=0.55 (silica gel, 1:1 hexane/ethyl acetate). $^1$NMR (DMSO-$d_6$): chemical shift (ppm) 7.12 (s, 1H, ArH), 6.07 (s, 1H, ArH), 4.45 (s, 2H, $CH_2$), 3.33-3.28 (m, 4H, $CH_2$), 2.87-2.82 (m, 4H, $CH_2$), 2.02-1.99 (m, 4H, $CH_2$). absorption maximum: 408 nm in methanol, emission maximum: 497 nm in methanol. MS: m/e 334.20.

Example 3

Synthesis of glutathione adduct of 2,3,6,7-tetrahydro-9-bromomethyl-1H,5H-quinolizino(9,1-gh)coumarin

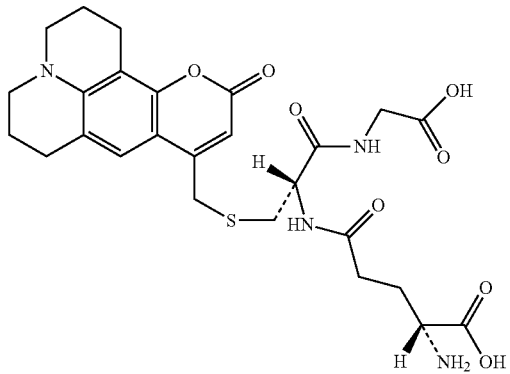

A mixture of 2,3,6,7-tetrahydro-9-bromomethyl-1H,5H-quinolizino(9,1-gh)coumarin (Example 2; 14 mg, 0.042 mmole), L-glutathione reduced (GSH, 20 mg, 0.065 mmol) and ammonium acetate (10 mg, 0.13 mmol) in 2 ml of methanol was stirred at room temperature for one day. The resulting crude reaction product was purified by silica gel column chromatography eluting with 20% water in acetonitrile. The combined desired fractions was lyophilized to give the glutathione product as a yellow-brown solid (10 mg, 43% yield). TLC: $R_f$=0.20 (silica gel, 2:8 water/acetonitrile). $^1$NMR ($D_2O$): chemical shift (ppm) 7.12 (s, 1H, ArH), 5.95 (s, 1H, ArH), 3.72 (s, 2H, $CH_2$), 3.71-1.82 (m, 20H, CH and $CH_2$) absorption maximum: 408 nm in water, emission maximum: 512 nm in water. MS: m/e 559.61.

Example 4

Synthesis of 2,3,6,7-tetrahydro-9-tosylmethoxy-1H, 5H-quinolizino(9,1-gh)coumarin

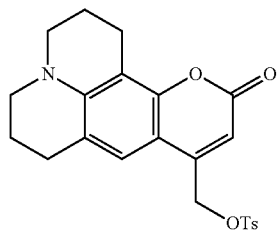

A mixture of 2,3,6,7-tetrahydro-9-bromomethyl-1H,5H-quinolizino(9,1-gh)coumarin (Example 2), in water and acetonitrile is stirred and heated. The solution is monitored by LC/MS until complete. The resulting 2,3,6,7-tetrahydro-9-hydroxymethyl-1H,5H-quinolizino(9,1-gh)coumarin is washed and separated in methylene chloride. The material is then dissolved in pyridine and tosylchloride. The reaction is stirred under heat and then washed and purified by silica gel chromatography.

Example 5

Synthesis of 3-(5-bromopentyl)furan-2,4(3H,5H)-dione

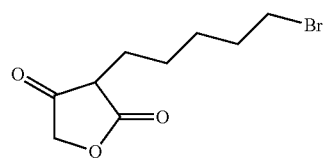 [SMILES: O=C1COC(=O)C1CCCCCBr]

To a solution of furan-2,4(3H,5H)-dione (500 mg, 5.0 mmol) in THF (10 ml) is added $K_2CO_3$ (2.5 g, 18.1 mmol) and the mixture is stirred at room temperature for 3 hours under nitrogen atmosphere. To the reaction mixture is added a solution of 1,5-dibromopentane (5.0 g, 21.7 mmol) in THF (10 ml), slowly over 30 minutes. It is then stirred vigorously at room temperature for one day. The reaction mixture is then partitioned between $CH_2Cl_2$ (100 ml) and saturated $NH_4Cl$ (50 ml). The organic phase is extracted with $CH_2Cl_2$ (3×50 ml), and the combined organic phase is washed with brine (50 ml), dried over $MgSO_4$ and concentrated. The resulting crude product is purified by column chromatography over silica gel eluting with 20% ethyl acetate to give a pure product.

Example 6

Synthesis of 3-bromopentyl-4-hydroxymethylquinolizinocoumarin

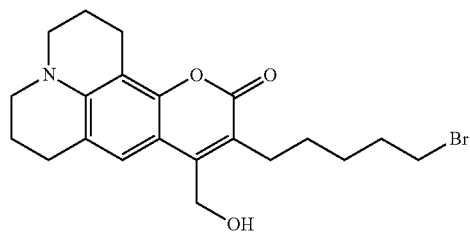 [SMILES: O=c1oc2c3c4c(cc2c(CO)c1CCCCCBr)CCCN4CCC3]

A mixture of 8-hydroxyjulolidine (200 mg , 1.06 mmol) and 3-(5-bromopentyl)furan-2,4(3H,5H)-dione (390 mg, 1.57 mmol) is stirred at ~90° C. under argon atmosphere. To this mixture is added a solution of aluminium chloride (400 mg, 3.0 mmol) in nitrobenzene (5 ml) and the whole reaction mixture is stirred at ~130° C. for 5 hours. After the reaction mixture is cooled to room temperature, it is purified by column chromatography over silica gel eluting with chloroform to give a desired product.

Example 7

Synthesis of 5-(4-hydroxymethylquinolizinocoumarin-3-yl)pentyltriphenylphosphonium bromide

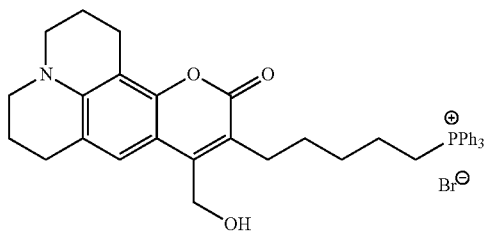

To a solution of 3-bromopentyl-4-hydroxymethylquinolizinocoumarin (Example 6) (0.20 mmol) in toluene (50 ml) is added triphenylphosphine (0.57 mmol) and the reaction mixture is heated under reflux for 5 hours. After cooling down to room temperature, the resulting precipitate is collected by filtration, washed with ether and dried in vacuo to give a product.

Example 8

Synthesis of 5-(4-bromethylmethylquinolizinocoumarin-3-yl)pentyltriphenylphosphonium bromide

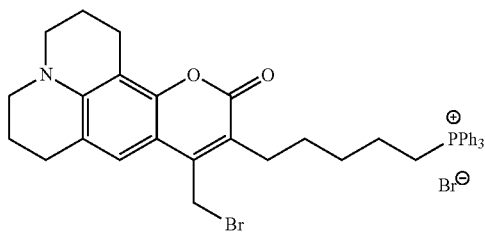

To a solution of 5-(4-hydroxymethylquinolizinocoumarin-3-yl)pentyltriphenylphosphonium bromide (0.16 mmol) in dry acetonitrile (30 ml) is added thionyl bromide (35 mg, 0.17 mmol) and the mixture is stirred at room temperature for one day. After the solvent is removed in vacuo, it is purified by column chromatography over silica gel first eluting with chloroform and the with 5% methanol in chloroform to give a desired product.

Example 9

General Protocol of Labeling Adherent Cells for Imaging

Cells are plated into 96-well microplates and allowed to recover for several hours or overnight. For testing effects of drugs on intracellular thiol/glutathione content, normal growth medium is removed and replaced with normal growth medium containing the test drug. The solution is incubated for several minutes to days. Growth medium is then removed and mixture is rinsed twice with DPBS with glucose/calcium/magnesium (Invitrogen #14287). The compound of Examples 1, 2 or 4 is added in DPBS (Invitrogen #14287), with a concentration up to 100 uM (typically 20 uM). The solution is incubated in a 37 degree C. incubator for 5-30 minutes (typically 30 minutes). Cells can be imaged after dye labeling.

Aldehyde fixation: The dye solution is removed and formaldehyde 3.7% (Sigma F1635, or higher quality) in DPBS (Invitrogen #14190) is added and incubated at room temperature in a fume hood for 30 minutes. The formaldehyde fixative is then removed and cells are rinsed with DPBS (Invitrogen #14190) twice. Cells are kept in PBS.

Where necessary, nuclear counterstain for cell identification is performed with a suitable nuclear stain which does not interfere with dye compound in fluorescence spectra. PBS is removed and TO-PRO-3 (Invitrogen T3605, 5 uM) is added with RNase (Invitrogen #12091-039, 1:1000) in PBS (Invitrogen #14190). The mixture is incubated at room temperature for 2 hours or longer, or at 4 degree C. for overnight. The counter-stain is then removed and, cells are rinsed twice with DPBS (Invitrogen #14190).

The material is imaged with a fluorescence microscope with filter set for Hoechst 33342 (e.g. Arrayscan VTI (Thermo Fisher Scientific/Cellomics) to acquire the images automatically).

To quantitate the images of cells stained with the Example compounds, one of the image analysis "BioApplcations" of Arrayscan VTI is used. The basic principle of the software is described as follows: Individual cells in an image are identified using the intensity profile of nuclear stain (e.g. TO-PRO-3). The regions derived from the identified nuclear region in individual cells is obtained ("CytoRing"). Pixel intensity of the dye in cells are measured in regions (Nucleus, and/or "CytoRing") defined by the cell identification method based on the nuclear counter stain. Cell-level data (intensity and other attributes of each cell in all acquired images) are then reported by the computer for further processing and analysis.

Example 10

Glutathione (GSH) is the Major Intracellular Target of the Example Compounds U-2 OS cells (ATCC HTB-96, human osteosarcoma cells) were plated in 10-cm dishes and incubated overnight in a 37 degree C. cell culture incubator. The cells were then treated with DL-Buthionine-(S,R)-sulfoximine (BSO, 4 mM in growth medium) for overnight (Control=no BSO treatment). The cells are rinsed cells 3 times with 10 mL of DPBS (Invitrogen #14287).

Labeling of cells: Example 2 (40 uM) in DPBS (Invitrogen #14287) was incubated at room temperature for 1 hour. The dye solution was removed and cells rinsed with DPBS (Invitrogen #14287) twice. The cells were scraped off the dish in the presence of DPBS and transferred to a 15 mL conical tube. The cells were pelleted by centrifugation—(5 min. at 5000 rpm, Centrific centrifuge, Fisher Scientific) and resuspended in DPBS, followed by pelleting cells by centrifugation for 5 min at 1000×g. The cells were resuspended in 170 µl DPBS and, to one half, 1 µl Protease Inhibitor (Sigma, P8340) was added, followed by 2 µl 1 M NEM for 30 min and 4 µl 1 M DTT for 30 min.

Figure 1:
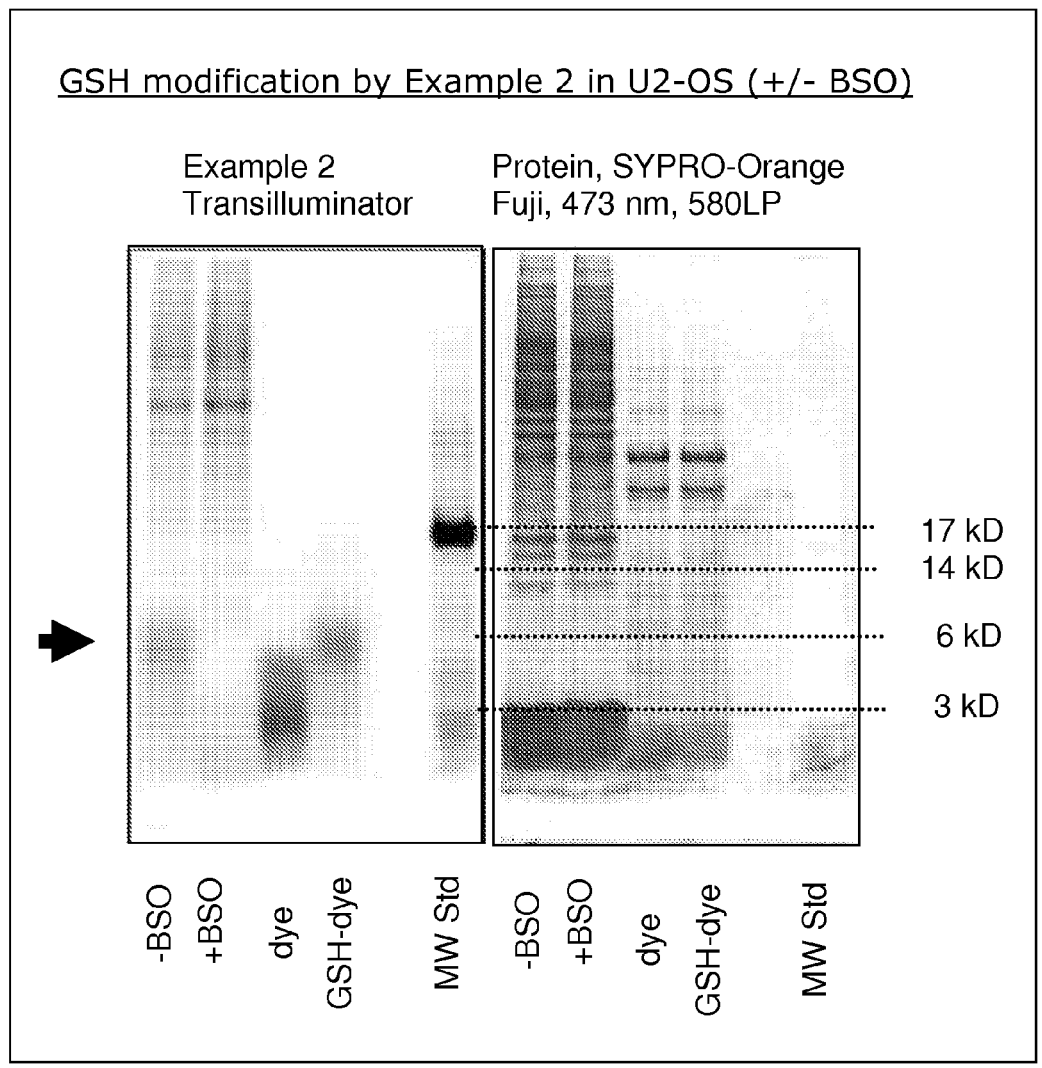
FIG. 1 shows Glutathione (GSH) is the major intracellular target of Example 2 in U-2 OS cells in 10 cm-dishes, (+/−) BSO 4 mM treatment, overnight and treatment with Example 2 (40 uM for 60 min). Example 3 included (lanes 3 & 4) for comparison.

Processed samples were resolved with SDS-PAGE (NuPAGE 12% Bis-Tris, Invitrogen, NP0342BOX) run in MES buffer (Invitrogen, NP0002). LDS sample buffer (NP0007) and Molecular weight standard (SeeBluePlus2 Prestained Standard LC5925) were obtained from Invitrogen. The gel was run for 55 min at 150 V. As controls the free dye (Example 2) and the GSH conjugate of this dye (Example 3) were run on the same gel. The gel was then scanned with a transilluminator (G-Box, Syngene) using a SP filter to visualize the fluorescent bands. After staining with SYPRO Orange (Invitrogen) total protein was observed with a FLA-3000 (Fujifilm) using for excitation 473 nm and for emission a 580 LP filter (See FIG. 1).

Figure 2:
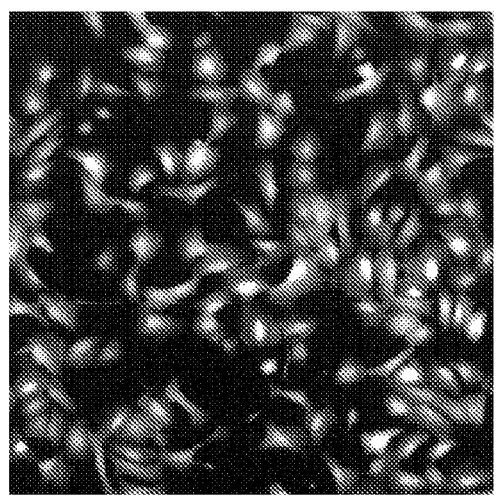
FIG. 2 shows U-2 OS cells staining of probes with similar staining pattern: overall staining of cells, including nuclear and cytoplasmic area. Images to illustrate staining patterns only, not scaled identically, not for comparison of stain intensity. Example 1: 405 nm/493 nm in MeOH and Example 2: 413 nm/515 nm in MeOH
Figure 2:
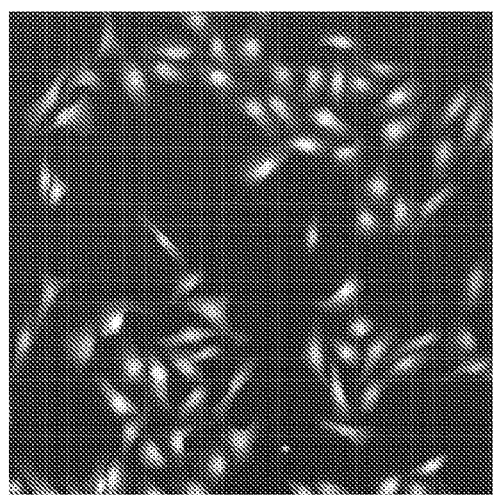
Figure 2:
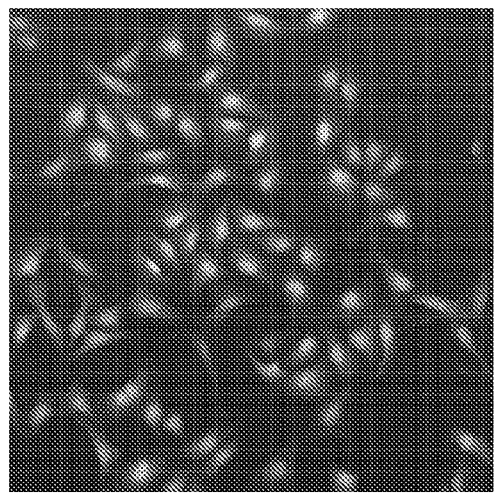
Figure 2:
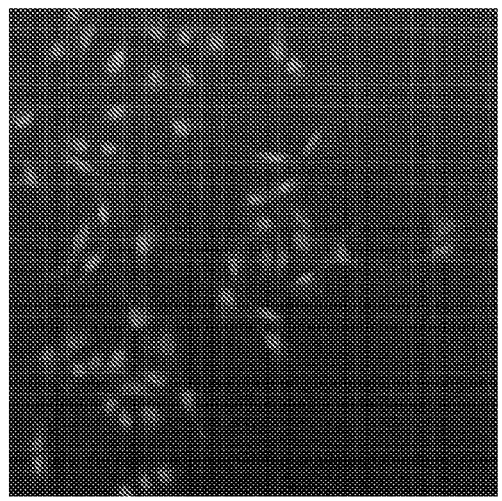

Both Example 1 and Example 2 give cellular staining patterns similar to that of 7-amino-4-chloromethylcoumarin (CMAC, Invitrogen C2110), or monochlorobimane (mBCl, Invitrogen M1381MP). The overall stain of the whole cell is prominent in nuclear area and diffuse stain in the cytoplasm, with low staining in the cell periphery (See FIG. 2).

Example 11

Combination with Antibodies

Live cells are incubated with Example 2 followed by fixation, permeablization, and immunocytochemistry using a primary antibody against GSH/GSSG (directly conjugated to a fluorophore that is spectrally resolvable (excitation >450 nm) from Example 2 or subsequent detection with fluorophore conjugated to secondary antibody). Example 2, used first in labeling protocol first binds available reduced glutathione (GSH) leaving only oxidized form (GSSG) for antibody to recognize in second part of protocol. This provides a semi-quantitative method for measuring total cellular glutathione and proportion of GSH/GSSG.

While the preferred embodiment of the invention has been illustrated and described, it will be appreciated that various changes can be made therein without departing from the spirit and scope of the invention.

What is claimed is:

1. A compound selected from the group consisting of 2,3,6,7-tetrahydro-9-bromomethyl-1H,5H-quinolizino(9,1-gh)coumarin and 2,3,6,7-tetrahydro-9-chloromethyl-1H,5H-quinolizino(9,1-gh)coumarin.

2. A coumarin compound of Formula (I) or a salt or tautomer thereof:

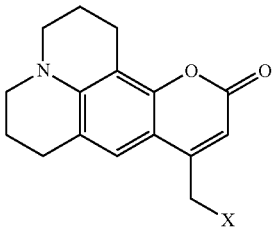

I wherein,
X is halo, a tosyl, brosyl or mesyl group.

3. The compound of claim 2, wherein X is halo.
4. The compound of claim 2, wherein X is bromo.
5. The compound of claim 2, wherein X is chloro.
6. The compound of claim 2, wherein X is a tosyl, brosyl or mesyl group.
7. A compound of Formula (I) or a salt or tautomer thereof:

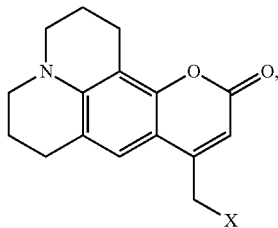

I wherein X is glutathione.

8. A method for detecting or quantifying a thiol compound in a sample, the method comprising:
   (a) contacting the sample with the coumarin compound of claim 2, to form a contacted sample;
   (b) incubating the contacted sample for an appropriate amount of time to form an incubated sample;
   (c) illuminating the incubated sample with an appropriate wavelength to form an illuminated sample; and
   (d) detecting fluorescent emissions from the illuminated sample;
   wherein the fluorescent emissions are used to detect or quantify the thiol compound in the sample.

9. The method of claim 8, wherein the sample comprises cells.

10. The method of claim 9, wherein the contacted sample is incubated for a sufficient amount of time for the coumarin compound to enter the cell.

11. The method of claim 8, wherein the sample comprises live cells, intracellular fluids, extracellular fluids, sera, biological fluids, biological fermentation media, environmental sample, industrial samples, proteins, peptides, buffer solutions biological fluids or chemical reactors, blood cells, immune cells, cultured cells, muscle tissue, neurons, extracellular vesicles; vascular tissue, blood fluids, saliva, urine, water, soil, waste water, sea water; pharmaceuticals, foodstuffs or beverages.

12. The method of claim 8, wherein the thiol compound reacts with the coumarin compound.

13. The method of claim 8, wherein the sample is immobilized on a polymeric membrane, within a polymeric gel, on a microparticle, on a microarray, on a silicon chip, on a glass slide, on a microwell plate, and on a microfluidic chip.

14. The method of claim 9, wherein the coumarin compound is substituted with a cationic group and the glutathione that is detected or quantified is present in the mitochondria of the cell.

15. The method of claim 14, wherein the cationic group comprises a triphenylphosphonium ion.

16. The method of claim 8, wherein the thiol compound comprises a cysteine residue.

17. The method of claim 8, wherein the thiol compound is glutathione.

18. The method of claim 8, further comprising a step of fixing the sample.

19. The method of claim 8, further comprising a step of permeablizing the sample.

20. The method of claim 8, further comprising a step of separating unbound coumarin compound.

21. The method of claim 8, further comprising a step of adding an antibody specific for the thiol compound after the incubating step.

22. A method of synthesizing the coumarin compound of claim 2 comprising:
   contacting 8-hydroxyjulolidine with ethyl 4-haloacetoacetate to form a reaction mixture;
   incubating the reaction mixture for a sufficient amount of time for the coumarin compound to form.

23. The method of claim 22, wherein the incubating step comprises heating the reaction mixture to at least 100° C.

24. The method of claim 22, wherein the reaction mixture further comprises a Lewis acid.

25. The method of claim 24, wherein the Lewis acid is aluminum chloride ($AlCl_3$).

26. A coumarin compound, selected from the group consisting of the following structures:
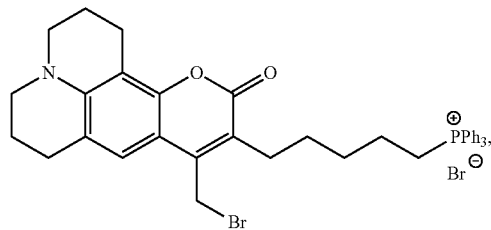
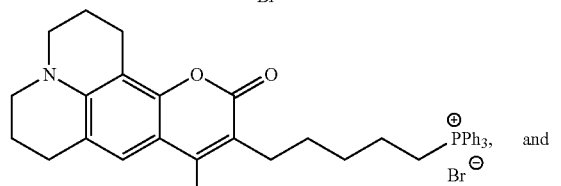 and
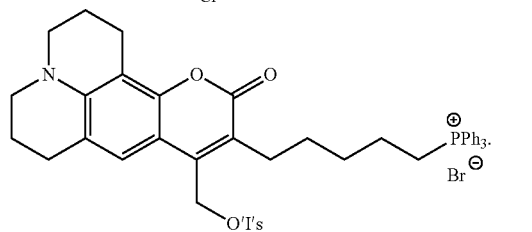
* * * * *